(12) United States Patent
Middleton et al.

(10) Patent No.: US 8,109,902 B2
(45) Date of Patent: Feb. 7, 2012

(54) SYSTEMS AND METHODS FOR MIXING FLUIDS

(75) Inventors: Lance Middleton, Trumbull, CT (US); Scott Reed, Monroe, CT (US); Jared Walkenhorst, Fairfield, CT (US)

(73) Assignee: Spine Wave, Inc., Shelton, CT (US)

( * ) Notice: Subject to any disclaimer, the term of this patent is extended or adjusted under 35 U.S.C. 154(b) by 221 days.

(21) Appl. No.: 12/581,971

(22) Filed: Oct. 20, 2009

(65) Prior Publication Data

US 2010/0042044 A1 Feb. 18, 2010

Related U.S. Application Data

(62) Division of application No. 10/803,214, filed on Mar. 18, 2004, now abandoned.

(51) Int. Cl.
*A61M 37/00* (2006.01)

(52) U.S. Cl. .......................................... 604/82; 604/416

(58) Field of Classification Search .................... 604/82, 604/416, 191, 90, 246; 366/336–341
See application file for complete search history.

(56) References Cited

U.S. PATENT DOCUMENTS

| | | | |
|---|---|---|---|
| 1,029,689 A * | 6/1912 | Kelley | 604/195 |
| 3,010,705 A | 11/1961 | Brown | |
| 3,526,391 A | 9/1970 | Church, Jr. | |
| 3,729,031 A | 4/1973 | Baldwin | |
| 3,860,218 A | 1/1975 | Hurlimann | |
| 4,743,229 A | 5/1988 | Chu | |
| 4,979,942 A | 12/1990 | Wolf et al. | |
| 5,425,580 A | 6/1995 | Beller | |
| 5,601,077 A * | 2/1997 | Imbert | 128/200.14 |
| 6,062,722 A | 5/2000 | Lake | |
| 6,234,196 B1 | 5/2001 | Fischer et al. | |
| 6,305,413 B1 | 10/2001 | Fischer et al. | |
| 6,592,251 B2 | 7/2003 | Edwards et al. | |
| 2002/0169422 A1 * | 11/2002 | Ahnblad et al. | 604/217 |

FOREIGN PATENT DOCUMENTS

WO 96/08227 A1 3/1996

* cited by examiner

*Primary Examiner* — Laura Bouchelle
(74) *Attorney, Agent, or Firm* — Hoffmann & Baron, LLP

(57) ABSTRACT

Improvements are provided for a syringe-to-syringe mixing system to improve the mixing characteristics of the system. In one embodiment, a mixing apparatus includes opposite fittings for mounting to a pair of syringes. The mixing apparatus defines a fluid passageway therethrough and includes a flow modifying element disposed within the passageway. The flow modifying element is configured to increase the flow velocity, disrupt the fluid flow or introduce turbulence into the fluid flow between the two syringes. In another embodiment, a nozzle element is disposed within the tip of the syringe, the element configured to increase the fluid flow therethrough. The nozzle element can be a nozzle insert removably mounted within the tip, or an integrally formed nozzle within the tip.

10 Claims, 9 Drawing Sheets

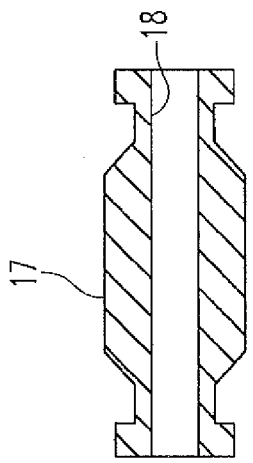
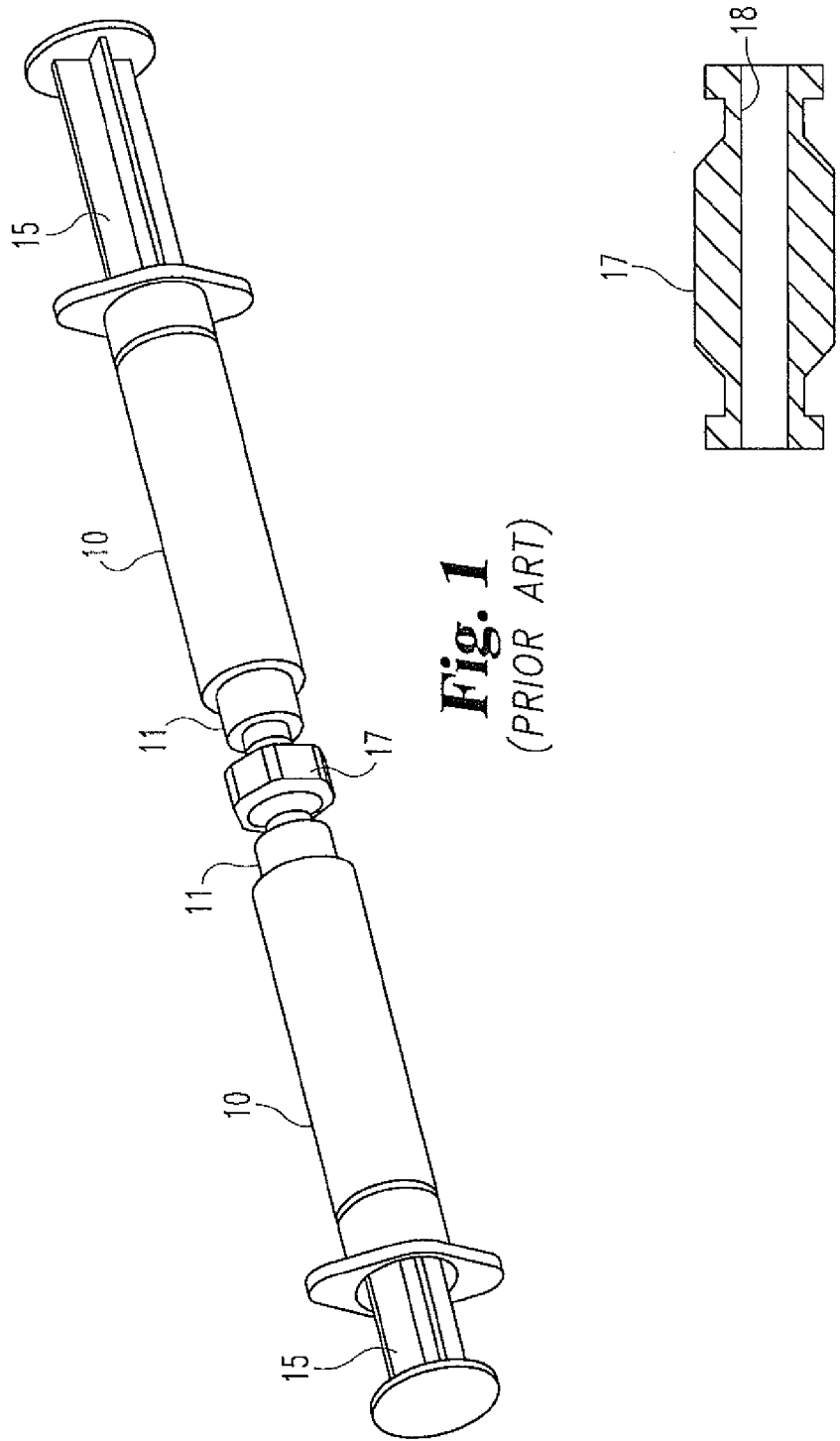
Fig. 1
(PRIOR ART)
Fig. 2
(PRIOR ART)

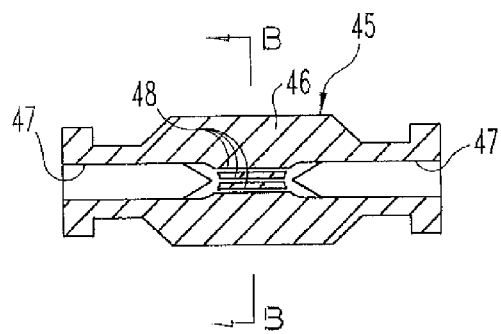 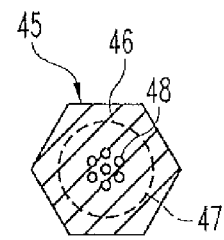
*Fig. 9a*  *Fig. 9b*
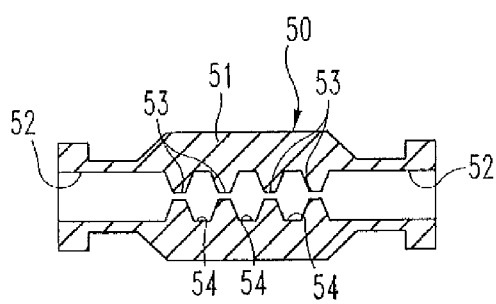 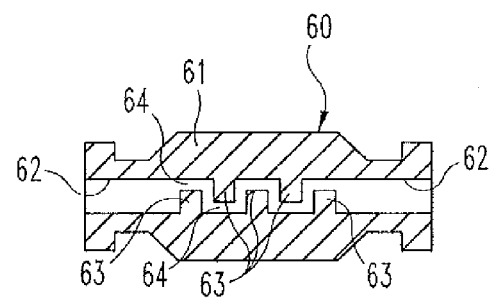
*Fig. 10*  *Fig. 11*
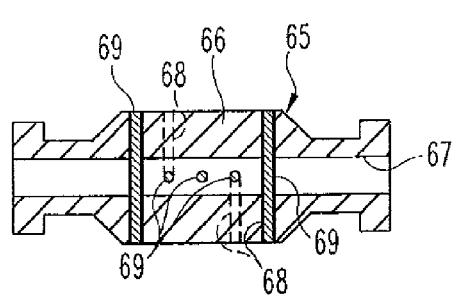 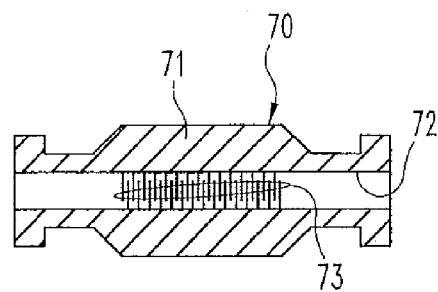
*Fig. 12*  *Fig. 13*

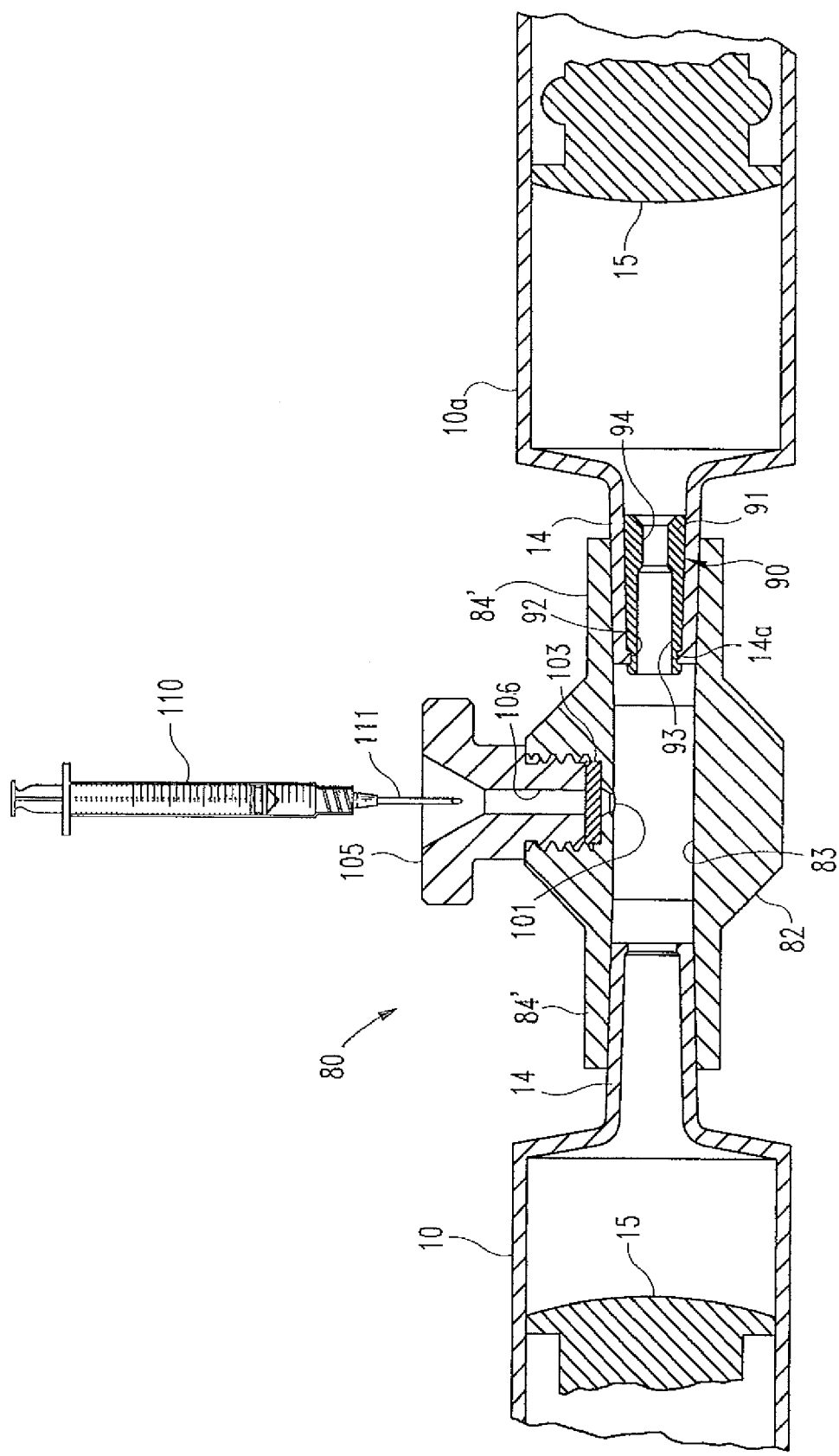

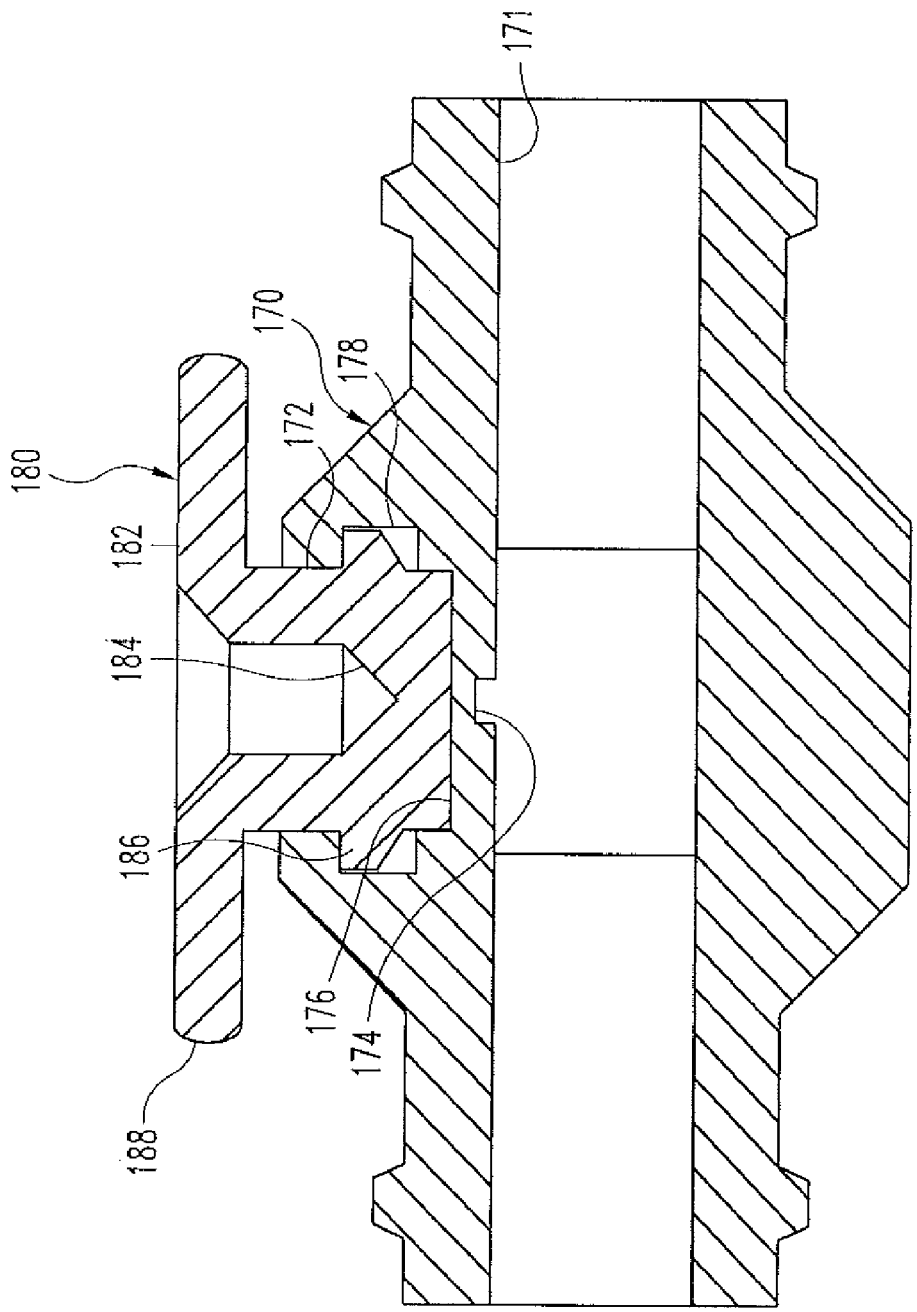

SYSTEMS AND METHODS FOR MIXING FLUIDS

CROSS REFERENCE TO RELATED APPLICATION

This application is a divisional of and claims priority to co-pending application Ser. No. 10/803,214, filed on Mar. 18, 2004, in the name of the same inventors, the entire disclosure of which is incorporated herein by reference.

BACKGROUND OF THE INVENTION

This invention relates to systems and methods for mixing fluids, and particularly medical fluids. More specifically, the invention relates to improvements in syringe-to-syringe mixing systems.

Several systems have been developed for on-site mixing and dispensing of multi-part medical and dental compositions. One system uses dual-cartridge syringes with static mix tips. These systems are generally not adequate for mixing polymers with high mix ratios. A further drawback is that a considerable amount of material is wasted in the mix tip, which may not be problematic for low cost fluid compounds but is potentially prohibitive for expensive materials, such as an injectable disc nucleus material.

Another known system, known as continuous flow systems, uses an electromechanical apparatus that drives a mix tip for controlled mixing of the fluids. Continuous flow systems are best suited for "assembly line" production and are excessive and too expensive for mixing single batches of fluid compounds.

A system that is very compatible for mixing small batches includes two medical syringes connected by an adapter so that fluids can be pushed back and forth between the syringes. One such prior system is depicted in FIGS. 1 and 2. Two syringes 10 are coupled by an adapter 17. The syringes can include Luer fittings 11 with similar fittings defined on the adapter. The adapter includes a uniform passageway 18 that allows flow of fluid from one syringe to the other as the plungers 15 are alternately depressed.

Syringe-to-syringe adapters like the adapter 17 have been used to couple a large reservoir syringe with a small dose syringe to simply transfer fluid from one to the other. These adapters have also been used to sequentially couple different syringes to a single syringe, each of the different syringes carrying a different fluid, or in some cases a granular compound to mix with the fluid in the single syringe. In some cases, the two syringes contain different fluids that must be thoroughly mixed. This mixing occurs by alternately depressing the plungers 15 of the opposing syringes 10 so that the fluids flow back and forth through the adapter. Once the fluid transfer or mixing is complete, the syringes are uncoupled and one or both of the syringes can be used as an applicator or injection device.

For many types of fluids and fluid compounds, this mixing approach is sufficient. For instance, many emulsions are prepared through syringe-to-syringe mixing. In these prior devices, the constant diameter passageway 18 in the adapter 17 allows full uniform flow of the fluid through the adapter, and the resultant mixture is complete enough for the particular medical application. One drawback of these prior systems is that they require relatively high plunger forces when mixing viscous fluids, which can lead to user fatigue. Another problem is that it is time consuming to achieve uniform distribution of micro-droplets within a fluid mixture.

Furthermore, in certain medical applications, the degree of mixing that can be accomplished with prior adapters, such as the adapter 17, is less than optimum. This problem manifests itself where high mix ratios are involved. For instance, certain injectable disc nucleus (IDN) compositions can have mix ratios between two constituents (i.e., polymer and cross-linker) greater than 10:1, and even greater than 100:1. The entire composition fails if the lower concentration constituent (such as the cross-linker in the case of an IDN) is not fully mixed within the other constituent (the polymer).

This mixing problem is also critical where the fluids combine to form a curable composition. In this case, as the different fluids are mixed they begin to cure, congeal or harden. For some materials, the curing time is sufficiently long so that the mixture can be cycled back and forth between the syringes enough times to ensure complete mixing of the constituents. For instance, many bone cements can be mixed using these types of prior devices.

However, the time necessary to achieve complete mixing is prohibitive for some curable materials that cure relatively quickly. If these types of materials are not dispensed in a timely manner, the mixture is worthless. For example, certain chemical compositions have been developed for the replacement of body tissues. One type of composition, known as hydrogels, is formed by mixing a polymer with a cross-linker. The resulting mixture starts to cure immediately when the constituents come into contact. For some hydrogels, the curing time is under two minutes. In these cases, it is imperative that the fluid mixing occur as quickly and completely as possible so that the surgeon has enough time remaining to inject the hydrogel at the surgical site.

The short curing times essentially prohibit mixing the constituents in any system other than a system that permits immediate injection of the mixture. In other words, syringe-to-syringe mixing is the most viable alternative for fluid compounds having short curing times.

Consequently, there is a need for a syringe-to-syringe system that yields complete mixing in mixing conditions that include one or more of the following parameters:
 High mix ratios (e.g., much greater than 10:1);
 Immiscible fluids;
 Rapidly curing polymers; and
 High viscosity fluids.

SUMMARY OF THE INVENTION

The present invention provides a syringe-to-syringe mixing apparatus that addresses these unresolved needs. In one embodiment, the mixing apparatus comprises an elongated body defining a passageway therethrough and configured at its opposite ends to engage a respective syringe thereat. The passageway communicates with the interior volume of each syringe so that fluid in each syringe can pass back and forth therebetween. In one feature of the invention, the mixing apparatus includes a flow modifying element disposed in the passageway that is configured to modify the flow of a fluid passing therethrough from syringe to syringe. The flow modifying element is configured to modify the fluid flow by increasing the flow velocity, disrupting the fluid flow or introducing turbulence.

In one preferred embodiment the flow modifying element is integrally formed in the body. In certain embodiments, the passageway defines a first flow area and the flow modifying element includes a restriction configured to increase the flow velocity therethrough, in which the restriction defines a second flow area less than the first flow area. In a specific embodiment, the first flow area is about five times greater than the second flow area.

The restriction assumes a variety of forms effective to disrupt the fluid flow and promote complete fluid mixing. For instance, the passageway and the restriction are substantially cylindrical in one embodiment, with the restriction constituting a nozzle. In other embodiments, the restriction is in the form of a slit, a multi-lobed opening, or a plurality of nozzles communicating between end portions of the passageway. In a further embodiment, the passageway includes a first portion adjacent one end of the passageway and a second portion adjacent the opposite end of the passageway, the first and second portions having longitudinal axes offset from each other. The restriction is then defined by an intersection between the first and second portions of the passageway.

In another aspect of certain embodiments of the invention, the body of the syringe-to-syringe mixing apparatus defines a mixing chamber between the flow modifying element and at least one of the opposite ends of the passageway. The passageway can be configured to receive a portion of the syringe tip therein, with the mixing chamber defined between the flow modifying element and the syringe tip when the tip is received within the passageway.

In some embodiments of the invention, the flow modifying element includes at least two nozzles in the passageway, each configured to increase the flow velocity therethrough. The body defines an intermediate mixing chamber between successive ones of the at least two nozzles. The intermediate mixing chamber defines a first flow area and each of the at least two nozzles defines a second flow area less than the first flow area.

In yet another aspect of the invention, the flow modifying element includes at least two baffles forming a serpentine flow path through the passageway. The flow modifying element may also include a plurality of pins traversing the passageway to disrupt the fluid flow through the mixing apparatus.

In some applications of the invention it is desirable to add a small quantity of an additional constituent to the fluid being mixed between the opposing syringes. Consequently, the invention contemplates means for introducing this constituent into the fluid flowing through the mixing apparatus. In one embodiment of the invention, the mixing apparatus body defines an orifice in communication with the passageway between the opposite ends thereof. The mixing apparatus is configured to receive a device for injecting the constituent through the orifice, such as a syringe.

In one feature of this embodiment, the orifice is a sealed orifice. The apparatus can further comprise a valve covering the orifice to prevent flow of the constituent therethrough. In one embodiment, the valve is a septum covering the orifice. The septum is adapted to be penetrated by a fluid introduction component, such as a syringe needle. In one specific embodiment, the septum is formed of a self sealing material, such as SILASTIC®, that seals around a needle when pierced and resiliently closes when the needle is removed. In another specific embodiment the septum includes a slit that is resiliently sealed by the septum material but can open upon pressure from the fluid introduction component.

The mixing apparatus is configured to accept the tips of opposing syringes. Thus, the passageway of the mixing apparatus body can be configured for a fluid-tight press-fit engagement with the tips of the syringes. The body can also include fittings at its opposite ends that are configured to engage the syringe. For instance, the fittings can be Luer fittings to engage complementary fittings on the syringes.

The present invention further contemplates an improvement to a syringe-to-syringe mixing apparatus comprising a nozzle element disposed within the tip of a syringe. The nozzle element defines a passageway therethrough in communication with the interior volume of the syringe and includes a restriction in at least one end of the nozzle element adjacent the interior volume of the syringe. The restriction is configured to increase the flow velocity therethrough. In one embodiment, restriction includes at least a portion of the passageway having a flow area that decreases toward the interior volume of the syringe.

In certain embodiments, the nozzle element is an insert configured to be mounted within the tip of the syringe. The insert includes a retaining flange at an opposite end of the nozzle element, wherein the retaining flange is configured to engage the end of the syringe tip. The insert can be configured to be inserted into the tip of the syringe through the interior volume of the syringe. In another embodiment, the nozzle element is integrally formed within the tip of the syringe.

The invention further provides in a syringe-to-syringe mixing system of the type having two syringes adapted to reciprocally pass fluid therebetween until mixed, a mixing apparatus comprising means for modifying the flow of fluid between the two syringes. This means is adapted to communicate with each of the two syringes and is preferably configured for disposition between the two syringes.

In one embodiment, this means for modifying the flow of fluid can include an elongated body, adapted at its ends to engage a corresponding one of the two syringes. The elongated body defines a fluid passageway in communication with the two syringes and a restriction within the passageway. The restriction can be in the form of a nozzle adapted to significantly increase the fluid flow velocity through the apparatus.

In another embodiment, the means modifying the flow of fluid is configured for disposition within one of the two syringes. In this embodiment, the means for modifying the flow of fluid can include a nozzle insert configured for engagement within the tip of one of the two syringes.

It is one object of the present invention to provide a syringe-to-syringe mixing system that efficiently mixes at least two constituents of a fluid composition. It is one particular object to provide a mixing system that can quickly and thoroughly mix the constituents of a composition that is "time sensitive", such as compositions that begin curing when mixed.

Another object is to provide a mixing system that can accept the introduction of small quantities of a constituent. A further object is to permit introduction of this constituent at any point in the mixing of the other constituents of the composition.

One benefit of the mixing apparatus of the present invention is that it can be used with traditional syringe-to-syringe mixing systems. Another benefit is that it provides complete and rapid mixing with minimal effort on the part of medical personnel. A further benefit of the present invention is that it is ideally suited for mixing self-curing compositions, or compositions that begin curing once the constituents come in contact with each other in appropriate ratios.

Other objects and benefits of the invention will become apparent upon consideration of the following written description, taken together with the accompanying figures.

DESCRIPTION OF THE FIGURES

FIG. 1 is perspective view of a syringe-to-syringe mixing system of the prior art.

FIG. 2 is a cross-sectional view of the adapter used in the mixing system shown in FIG. 1.

FIG. 9a is a side cross-sectional view of yet another alternative mixing apparatus for use in the mixing system shown in FIG. 3.

FIG. 9b is an end cross-sectional view of the nozzle configuration for a mixing apparatus shown in FIG. 9a, the cross-sectional view being taken along line B-B in FIG. 9a.

FIGS. 10-13 are side cross-sectional views of other alternative mixing apparatus for use in the mixing system shown in FIG. 3.

FIG. 15 is side cross-sectional view of the mixing apparatus shown in FIG. 14 in its assembled configuration.

FIG. 20 is a side cross-sectional view of a mixing apparatus with a one piece septum.

DESCRIPTION OF THE PREFERRED EMBODIMENTS

Figure 3:
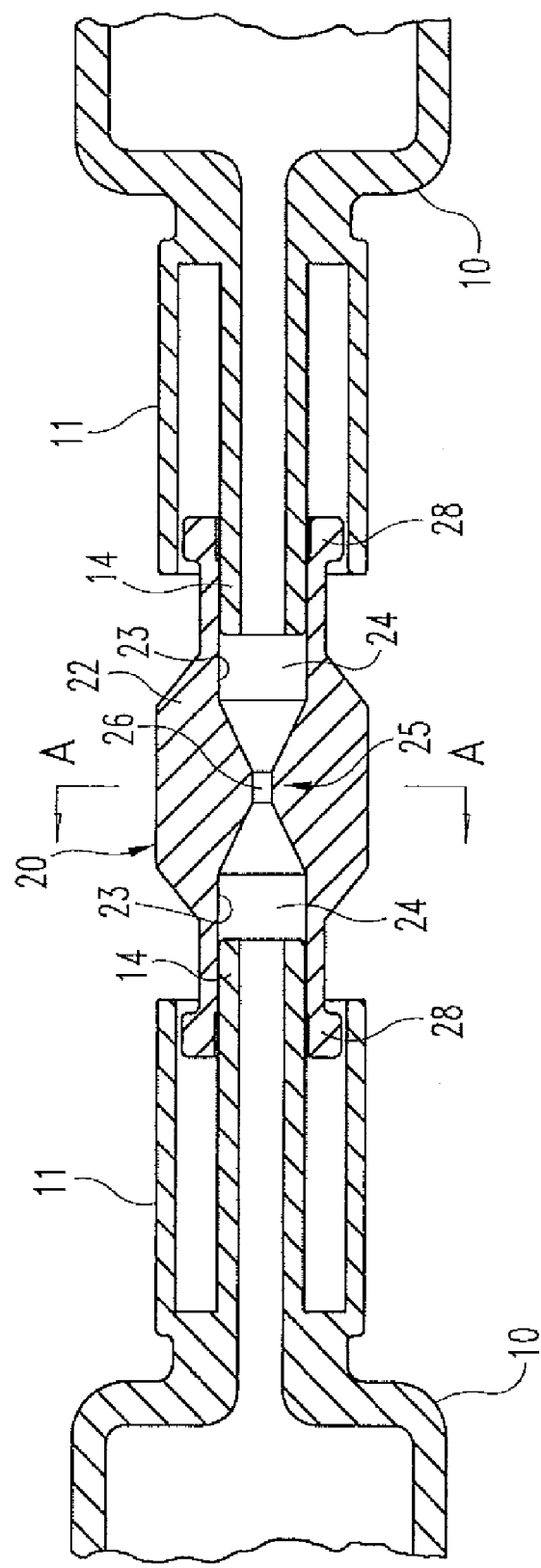
FIG. 3 is a side cross-sectional view of a syringe-to-syringe mixing system in accordance with one embodiment of the present invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates a mixing apparatus for use with a pair of syringes, such as the syringes 10 shown in FIG. 1. The mixing apparatus can be configured to mate with any syringes, such as by a press-fit engagement with the syringe tip, by Luer connection or other suitable means. As shown in FIG. 3, the syringe 10 can include a Luer fitting 11 with a fluid dispensing tip 14 extending concentrically therethrough. In accordance with one embodiment of the invention, a mixing apparatus 20 is connected between the two syringes. The apparatus 20 includes an elongated body 22 that defines a passageway 23 therethrough. The passageway 23 extends through fittings 28 at the opposite ends of the body. The fittings are configured to mate with either or both of the syringe Luer fitting 11 or tip 14. Preferably, the fittings 28 are configured to form a fluid tight engagement between the passageway 23 of the mixing apparatus and the dispensing tip 14 of the syringe. The exterior of the elongated body 22 can be configured to define a gripping surface to facilitate engagement of the apparatus to the syringes.

The passageway 23 is initially sized to receive the syringe tip 14 at the opposite ends of the mixing apparatus 20. In accordance with one feature of the invention, a flow modifying element 25 is disposed within the passageway. The flow modifying element is configured to modify the flow of a fluid through the passageway, such as by increasing the flow velocity, disrupting the fluid flow or introducing turbulence. In accordance with the embodiment of the invention shown in FIG. 3, the flow modifying element 25 includes a decrease in the size of the passageway to a nozzle 26 within the body 22. The term "nozzle" as used herein refers to structure that produces an increase in the velocity of fluid passing through the nozzle. In one particular embodiment, the passageway and nozzle have circular cross-sections, with the passageway gradually decreasing in diameter from the fittings 28 to the nozzle 26. The flow modifying element 25 or nozzle 26 can be integrally formed in the body 22 or can be a separate component that is inserted and fixed within the passageway 23.

The engagement between the syringe tip 14 and the fittings 28 of the mixing apparatus is configured to provide a mixing chamber 24 on each side of the nozzle 26. The nozzle operates to increase the flow velocity of fluid passing therethrough. The increase in cross-sectional area from the nozzle to the mixing chambers 24 preserves the greater fluid shear rates generated by the nozzle. A significant amount of fluid mixing occurs in the mixing chambers 24, but fluid mixing continues as the fluid is pushed from one syringe to the other.

In accordance with one feature of this embodiment, the length of the nozzle is comparatively short relative to the length of the mixing chambers 24 and passageway 23. Keeping the length of the nozzle to a minimum reduces the force that must be applied to drive the fluid through the nozzle. In a specific embodiment, the length of the nozzle is about twice its effective diameter. The nozzle 26 in this embodiment has an effective diameter of about 0.05 inches, and a length of about 0.1 inches. The passageway 23 has an effective diameter that is about five times greater than the nozzle diameter.

Other embodiments of the mixing apparatus include different nozzle configurations for the flow modifying element that do not employ as gradual a change as the embodiment of FIG. 3. For example, the embodiments illustrated in FIGS. 4-8 provide a more abrupt change in flow diameter. This abrupt change may be less efficient from a thrust perspective, but provides an efficient nozzle with non-laminar flow from a mixing perspective.

Figure 4:
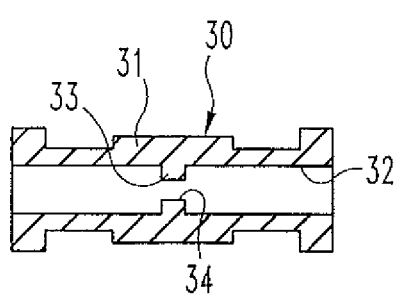
FIG. 4 is a side cross-sectional view of a mixing apparatus for use in the mixing system shown in FIG. 3.
Figure 5:
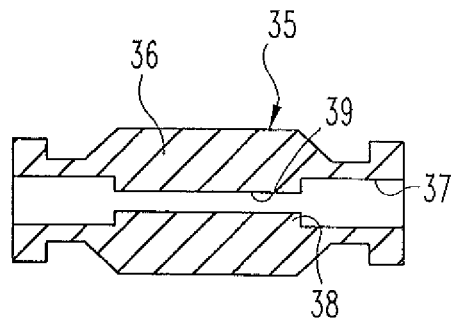
FIG. 5 is a side cross-sectional view of an alternative mixing apparatus for use in the mixing system shown in FIG. 3.

The mixing apparatus 30 shown in FIG. 4 includes a body 31 that defines a passageway 32 therethrough. A restriction 33 in the interior of the body creates a nozzle opening 34 in the passageway 32. This nozzle constriction serves the same purpose as the nozzle 26 described above. The embodiment shown in FIG. 5 is similar to that of FIG. 4, except that the length of the nozzle restriction has been increased. Thus, the mixing apparatus 35 of FIG. 5 includes a body 36 that defines the passageway 37 and the restriction 38. The resulting nozzle 39 extends over a significant portion of the length of the apparatus 35.

Figure 6:
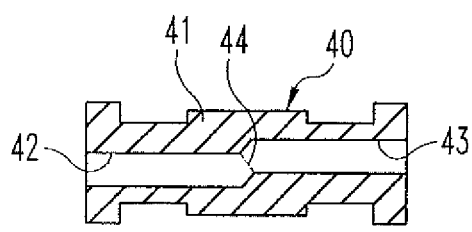
FIG. 6 is a side cross-sectional view of yet another alternative mixing apparatus for use in the mixing system shown in FIG. 3.

In the embodiment shown in FIG. 6, the nozzle is formed by the intersection of offset passageways. The mixing apparatus 40 includes a body 41 that defines two passageways 42, 43 from either end of the body. The passageways are offset but intersect at their inner extent. This intersection forms the nozzle 44. It should be understood with respect to each of the embodiments of FIGS. 4-6 that the passageways are configured like the passageway 23 to form a fluid-tight engagement with the syringe tip 14 and to provide a mixing chamber, such as the chamber 24, adjacent each syringe tip.

Figure 7:
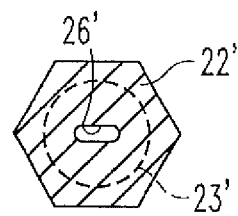
FIG. 7 is an end cross-sectional view of a further nozzle configuration for a mixing apparatus for use in the mixing system shown in FIG. 3, the cross-sectional view being taken along line A-A in FIG. 3.
Figure 8:
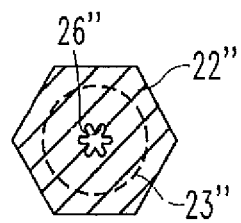
FIG. 8 is an end cross-sectional view of a still further nozzle configuration for a mixing apparatus for use in the mixing system shown in FIG. 3, the cross-sectional view being taken along line A-A in FIG. 3.

Variations in the configuration of the nozzle 26 (FIG. 3) are further illustrated in FIGS. 7 and 8. As indicated above, the nozzle 26 is circular in cross-section. As shown in FIG. 7, the nozzle 26' within a body 22' can be slit-shaped. The height of the slit 26' can be less than the effective diameter of the nozzle 26, although the effective area can be the same between the two nozzle variations. As a further alternative, a nozzle 26" can be multi-lobed, as depicted in FIG. 8. Each lobe of the nozzle can act as a miniature nozzle to locally increase the fluid flow relative to the central portion of the lobed nozzle. Thus, this approach can produce a fluid velocity gradient that can enhance mixing.

In a variation of the lobed nozzle concept, the flow modifying element for a mixing apparatus 45 of FIGS. 9a-b includes a plurality of miniature nozzles 48 defined in the body 46 at the interior of the passageway 47. These nozzles 48 produce several fluid "jets" that disperse within the mixing chambers to produce turbulent mixing.

In another approach, the flow modifying element includes a series of baffles interposed in the fluid flow path between the syringes. For example, as depicted in FIG. 10, the body 51 of a mixing apparatus 50 defines a passageway 52 therethrough that is interrupted by a series of restrictions or nozzles 53. The nozzles 53 form a series of intermediate chambers 54 so that the fluid is alternately restricted and expanded as it flows through the apparatus. As depicted in FIG. 10, the restrictions and intermediate chambers are uniform and cylindrical. Alternatively, the nozzles 53 and intermediate chambers 54 can form a spiral volume through the body 51.

The mixing apparatus 60 shown in FIG. 11 includes a series of alternating restrictions 63 that constitute the flow modifying element. The restrictions form a serpentine path for the fluid flow through the passageway 62 defined in the body 61. The restrictions 63 also define a reduced area 64 that operates as a nozzle to accelerate the fluid velocity. The restrictions 63 can take on a variety of forms, such as a wall across a chord of the circular area of the passageway 62.

The embodiments shown in FIGS. 12 and 13 rely upon flow modifying elements interposed in the passageway that disrupt the fluid flow. The mixing apparatus 65 shown in FIG. 12 includes a body 66 that defines a passageway 67 therethrough. The passageway may have a uniform cross-section throughout. The body further defines a plurality of bores 68 that at least open into the passageway 67, but preferably extend entirely through the body. The bores are oriented transverse to the length of the passageway, preferably, but not necessarily, at right angles to the passageway. The bores 68 support pins 69 that extend through the passageway 67. As illustrated in FIG. 12, the pins can be disposed at various angular orientations about the axis of the passageway. The pins 69 are preferably press-fit within the bores 68 to form a fluid-tight engagement. The pins may have an effective width within the fluid flow path that is significantly smaller than the effective diameter of the path. In a specific embodiment, the pins have a width of about $1/10^{th}$ the flow path diameter.

The pins have an effective width that is sufficient to disrupt the fluid flow through the passageway, but not so large that they greatly increase the flow resistance of the mixing apparatus. The pins generate eddies downstream of the pins with enough flow velocity through the passageway, which help mix the fluid constituents. Although the embodiment illustrated in FIG. 12 only includes five pins, greater numbers at smaller angular increments are contemplated.

The mixing apparatus 70 shown in FIG. 13 employs a similar concept. The body 71 of the apparatus supports a brush array 73 within the passageway 72. The brush array 73 includes small diameters pins or needles, but relies upon a large number across the flow path to produce desirable mixing characteristics.

In using the apparatuses shown in FIGS. 3-13, each syringe 10 contains one of the two fluid constituents. The syringes are at most only half-filled with their respective fluids. Where the mixing ratios are high, the volume of fluid in one syringe may be significantly greater than the volume in the other. Once air is purged from each syringe, any one of the mixing apparatuses in FIGS. 3-13 can be engaged to one of the syringes. The plunger is depressed to push fluid into the passageway of the mixing apparatus until a meniscus is formed at the open end of the passageway. The second syringe can then be engaged to the mixing apparatus. In addition, a device can be provided for injecting another constituent in small quantities, as described in more detail herein.

Fluid mixing occurs by alternately depressing the plungers 15 of the two syringes. The speed and number of alternating plunger movement depends upon the type of material being mixed. For some polymer compositions, ten cycles in ten seconds is sufficient for complete mixing of the fluid constituents.

The mixing adapters depicted in the figures are all "in line", meaning that the longitudinal axes of the syringes and the mixing apparatus are coincident. While this arrangement is believed to be optimum, it is possible to configure the mixing apparatuses to mate with non-aligned syringes. With this alternative configuration, at least a portion of at least one of the mixing chambers will be configured to change the direction of the fluid flow into the non-aligned syringe.

In the embodiments of the invention illustrated in FIGS. 3-13, the fluid mixing occurs primarily in the body of the mixing apparatuses. In these apparatuses 20, 30, 35, 40, 45, 50, 60, 65 and 70, mixing chambers 24 are defined within the central passageway as the volume between the restriction or nozzle and the tip 14 of the syringe. Fluid mixing occurs throughout the system, but the most intense fluid mixing occurs in these mixing chambers due to their proximity to the flow modifying element.

The present invention contemplates an alternative embodiment in which most of the fluid mixing occurs in the syringes themselves. In one exemplary embodiment shown in FIGS. 14-15, a mixing apparatus 80 is coupled between two syringes 10, which can be conventional syringes as discussed above. The mixing apparatus 80 includes a body 82 that defines a passageway 83 therethrough. The fittings 84 shown in FIG. 14 at the ends of the body can be similar to the fittings 28 of the embodiment discussed above with reference to FIG. 3. Alternatively, the fittings can be configured for a press-fit only, such as the fittings 84' shown in FIG. 15.

In accordance with this alternative embodiment, a nozzle insert 90 is inserted into the tip 14 of at least one of the syringes 10. As best seen in FIG. 15, the nozzle insert 90 is formed by an elongated tubular body 91 that is configured for a fluid-tight engagement within the syringe tip 14, such as by a press-fit. In certain embodiments, the insert 90 includes a retaining flange and groove feature 92 that interlocks with a circumferential ridge 14a typically formed on the syringe tip 14. This interlocking engagement can be sufficient to hold the nozzle insert 90 within the tip 14, even where the insert has only a close running fit (rather than a press fit) within the syringe tip.

Again as seen in FIG. 15, the nozzle insert 90 defines a passageway 93 therethrough. This passageway includes a restriction 94 at the inner end of the nozzle insert—i.e., immediately adjacent the interior volume of the syringe when the insert is positioned within the syringe tip 14. This restriction 94 serves to increase the flow velocity as the fluid mixture enters the syringe 10a. In the preferred embodiment, the restriction 94 defines a circular flow area. However, the restriction can assume other configurations, such as the configurations depicted in FIGS. 7, 8 and 9b.

Figure 16A:
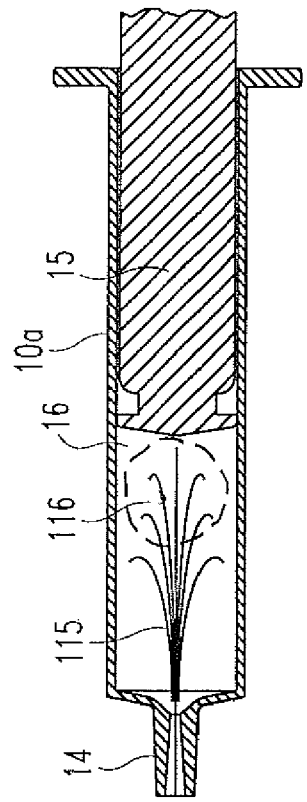
FIG. 16a is representation of fluid flow patterns into a syringe using prior syringe-to-syringe mixing techniques.
Figure 16B:
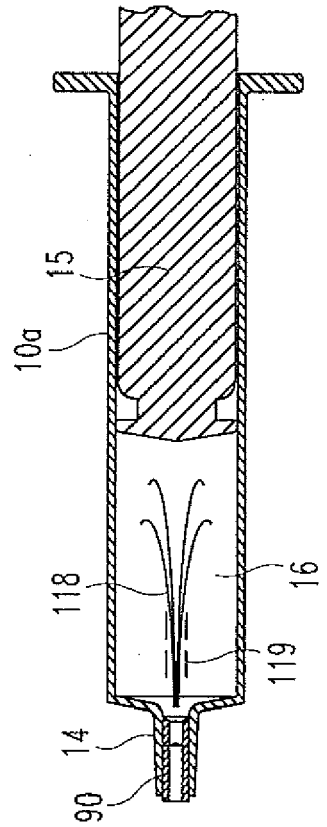
FIG. 16b is a comparative representation of fluid flow patters into a syringe using the syringe-to-syringe mixing apparatus of FIGS. 14-15.

The benefits of this nozzle insert 90 can be discerned by the comparison in FIGS. 16a-b. The depiction in FIG. 16a represents fluid flow through the standard syringe tip 14 directly into the syringe interior volume. As the plunger 15 is withdrawn, the fluid exits the tip 14 in a fluid stream 115 having a velocity V1. As the plunger moves farther from the tip 14, a region 116 of poor fluid circulation arises as the fluid stream 115 decays into laminar flow behind the plunger.

In contrast, FIG. 16b depicts the fluid flow through the nozzle insert 90. The fluid stream 118 discharged from the insert 90 has a much higher flow velocity V2 than the standard configuration in FIG. 16a. This greater flow velocity means that the high velocity fluid stream extends farther into the syringe 10a even as the plunger 15 is withdrawn. In one embodiment, the velocity V2 is five times greater than the velocity V1 achieved in a conventional syringe-to-syringe mixing system. Ideally, the size of the restriction 94 in the nozzle insert 90 is calibrated to that the fluid stream 118 does not deteriorate into laminar flow until the plunger has reached its maximum withdrawal, if at all. The high velocity fluid stream 118 passes through a virtual "wall" of stationary or slower moving fluid 119 around the stream 118. This results in high shear rates, which ultimately results in greater mixing than can be accomplished with the conventional syringe-to-syringe system depicted in FIG. 16a.

Figure 17:
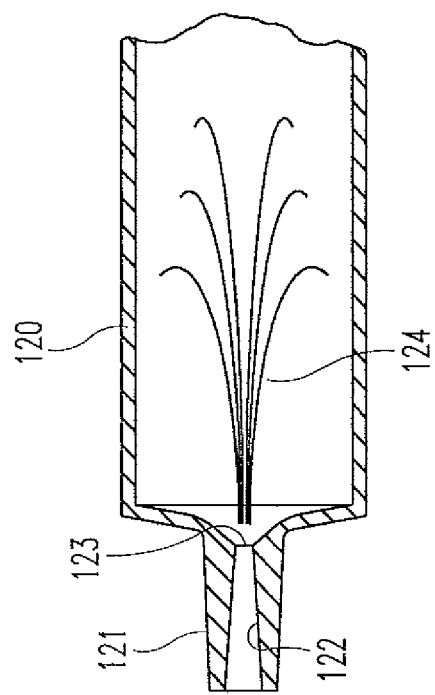
FIG. 17 is a side cross-sectional view of a syringe modified in accordance with one embodiment of the present invention.

In an alternative approach, the restriction can be integrated into the syringe tip itself, as illustrated in FIG. 17. A syringe 120 can include a tip 121 that defines a fluid passageway 122. The interior end of the passageway defines a nozzle 123 to produce the high velocity jet flow 124 contemplated in FIG. 16b. In the preferred embodiment, the passageway 122 is tapered toward the nozzle 123 to gradual restrict the fluid flow being drawn into the syringe 120. This modified syringe tip 121 achieves the same beneficial fluid flow characteristics discussed above relative to the nozzle insert 90.

While the preferred embodiment contemplates a restriction 94 that produces an increase in flow velocity, another alternative is to disrupt the fluid flow into the syringe. Thus, the restriction can be replaced by the flow modifying elements depicted in FIGS. 12-13. Introduction of the pins 69 or needles 73 disrupts the fluid flow, producing turbulence of eddies that may improve fluid mixing within the syringe.

Returning to FIGS. 14 and 15, a further feature of the invention is the provision of a septum for injection of a fluid constituent into the mixing apparatus 80. In particular, the body 82 defines a septum bore 100 that intersects the passageway 83 through the body. The bore terminates in a small diameter orifice 101 that is sized to receive a hypodermic needle. The orifice 101 is covered by a septum 103 that is formed of a self-sealing material. In particular, the septum 103 is configured to be penetrated by a needle 111 attached to a syringe 110 carrying an additional fluid constituent. A set screw 105 is threaded into the septum bore 100 to press and retain the septum within the bore and keep it taut for penetration by the needle 111. The septum can be formed of a conventional self-sealing material, such as SILASTIC®, or may include a slit therethrough as is known in the art.

The septum orifice 101 provides means for introducing an additional fluid into a mixture, where one or more other fluids are contained within the syringes 10, 10a. In addition, the orifice 101 supplies an avenue for the introduction of a low ratio fluid constituent. For instance, where the mix ratio is 100:1 and above, the volume of one constituent is extremely small compared to the volume of the constituent contained in one of the syringes 10. Carrying this low ratio fluid in one of the syringes 10 may not result in a complete mixing of the two fluids. Thus, the introduction of the low ratio fluid directly into the fluid flow passing through the mixing apparatus 80 ensures that the low ratio fluid will be entrained within the higher volume fluid.

Although the septum feature is depicted in combination with the nozzle insert, the septum can be integrated into any of the mixing apparatuses shown in FIGS. 3-13. In that case, the septum orifice 101 can intersect the nozzle (e.g., the nozzle 26) or one of both of the mixing chambers 24 or the syringe 10.

The septum provides a ready interface for needle injection of a fluid into the mixing stream. Alternatively, the septum bore 100 can be used as a reservoir to hold a fluid constituent. The orifice 101 can be sized and arranged within the body 82 to act as a venturi orifice. As fluid flows past the orifice 101, the reduced pressure will draw fluid from the bore/reservoir 100 to mix with the fluid passing through the passageway 83. Optimally, where the orifice serves as a venturi opening, the orifice 101 is positioned at a narrowing in the passageway, such as at the nozzle 26 of the apparatus 20 shown in FIG. 3, so that the increased flow velocity will rapidly draw the fluid into the flow.

Figure 14:
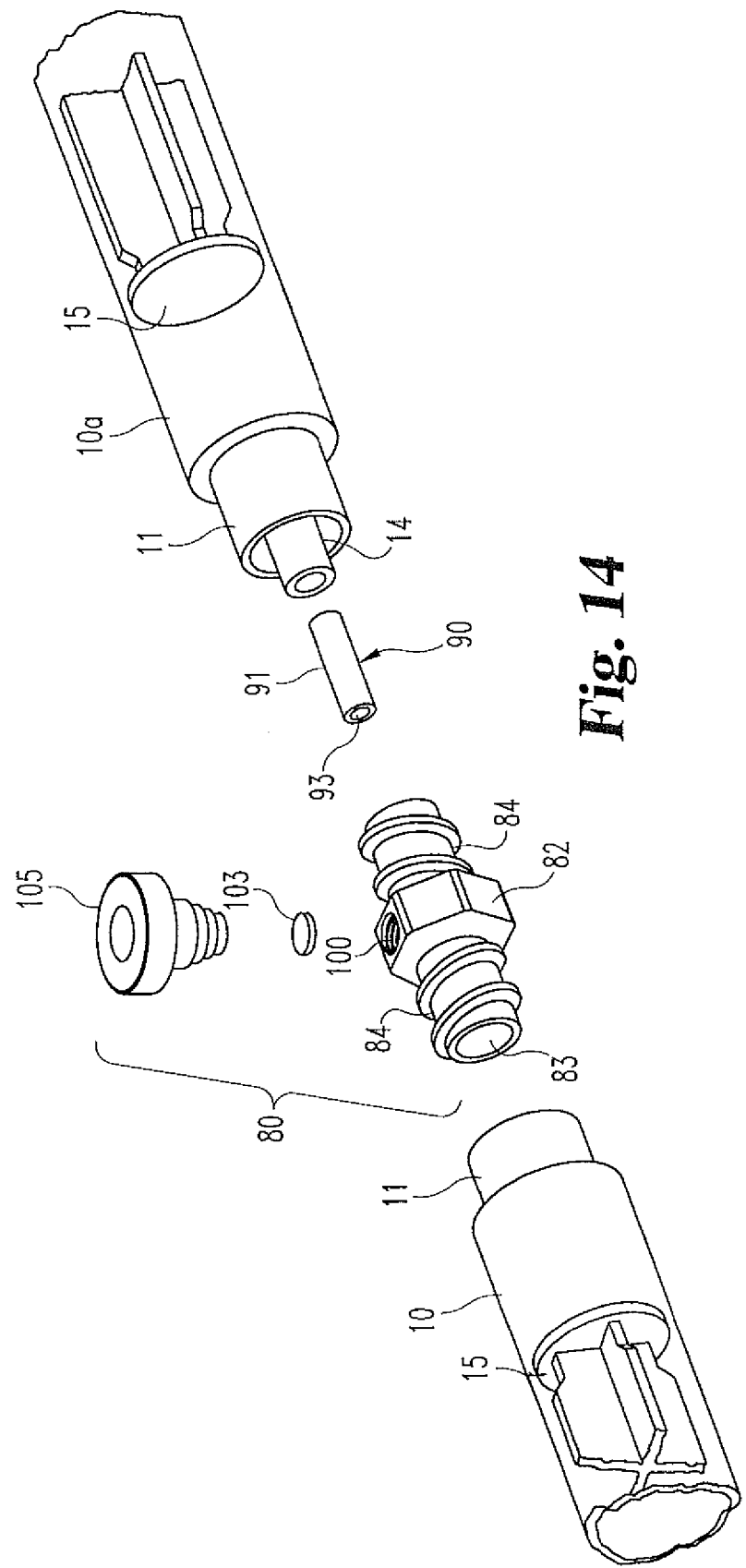
FIG. 14 is an exploded perspective view of a mixing apparatus in accordance with a further embodiment of the invention.

In one application of the mixing apparatus 80 shown in FIGS. 14-15, the syringes 10, 10a are 5 ml syringes. Syringe 10 is filled with 4.5 ml of a polymer used to form an IDN composition. The mixing apparatus 80 is engaged to the syringe 10a and air within the syringe and apparatus is purged.

Figure 18:
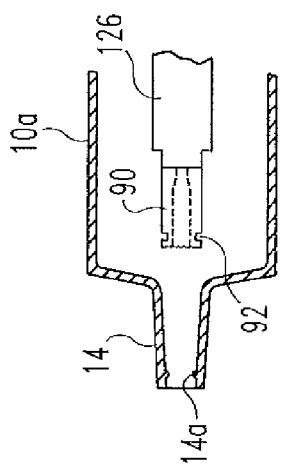
FIG. 18 is a partial cross-sectional view of a nozzle insert being positioned within the tip of a syringe to form the mixing apparatus shown in FIGS. 14-15.

Next, the plunger 14 is removed from the other syringe 10a and the nozzle insert 90 is mounted on an insertion tool 126. As depicted in FIG. 18, the insertion tool is used to push the nozzle insert 90 into the syringe tip 14 from the inside of the syringe. This approach is particularly necessary where the interior of the tip is inwardly tapered away from the barrel of the syringe. The insert is pushed into the tip until the retaining flange and groove 92 snap around the ridge 14a at the interior of the distal end of the tip. The plunger 14 is then reinserted into the syringe and the second syringe 10a is attached to the mixing apparatus 80

About 2 ml of the polymer in the first syringe 10 is transferred into the second syringe 10a and that syringe is detached from the mixing apparatus. Air is again purged from both syringes with care given to ensuring that a positive meniscus is formed at the tip of the second syringe 10a and at the open end of the mixing apparatus. The assembly is completed by re-attaching the second syringe to the mixing apparatus.

The polymer in the second syringe 10a is then shifted back to the first syringe 10 and the filled assembly is placed aside until the final IDN composition is needed for introduction into the patient. When that point arrives, a third syringe 110 loaded with a cross-linker is provided. The needle 111 punctures the septum 103 and the full pre-measured quantity of cross-linker is injected into the mixing apparatus 80. This solution is then mixed by cycling the syringe plungers 14 back and forth for ten cycles in 7-10 seconds, ending with the entire volume in the first syringe 10. The surgeon then has a limited amount of time to inject the mixed IDN composition into the patient's disc, under 1½ minutes for certain compositions. The first syringe is detached from the mixing apparatus and an injection needle mounted to the syringe to accomplish the disc injection.

Figure 19:
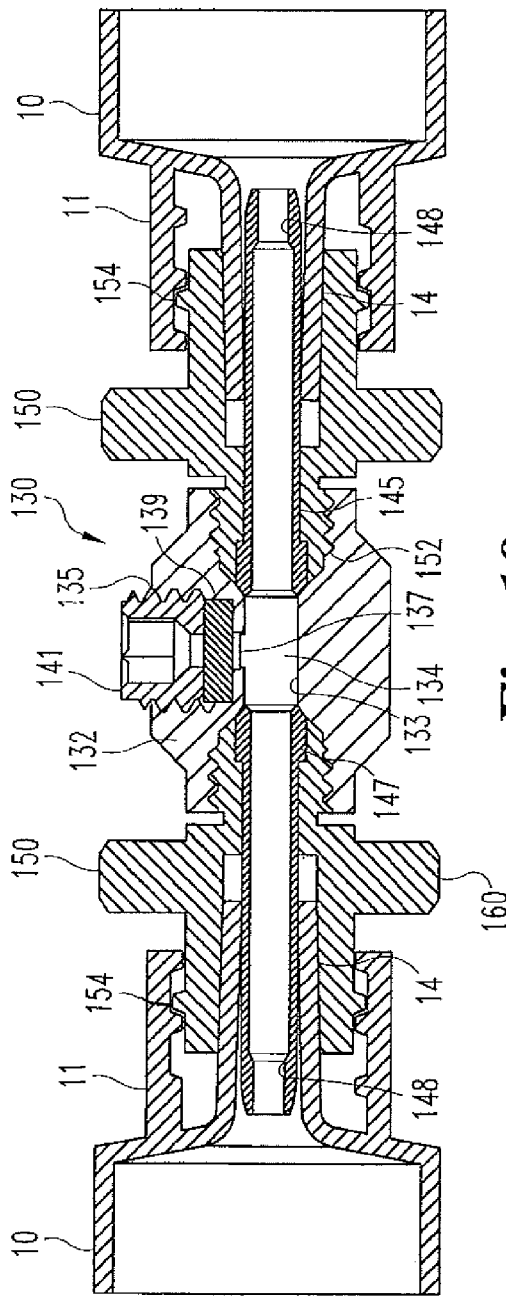
FIG. 19 is a side cross-sectional view of a mixing apparatus of still another embodiment of the invention.

An alternative mixing apparatus 130 is illustrated in FIG. 19. A body 132 defines a passageway 133, a septum bore 135 and an orifice 137. A septum 139 is contained within the bore by a set screw 141. The apparatus 130 includes a nozzle insert 145 that is mounted within the tip 14 of the two syringes 10. The nozzle insert includes a head 147 that is trapped within the body 132, closing the passageway 133 to define a chamber 134. The nozzle inserts 145 are much longer than the insert 92 of FIGS. 14-15, but include the same restriction feature 148. Unlike the nozzle insert 90, the inserts 145 are configured to be inserted into the syringe tips 14 from the outside of the syringe, rather than from the inside, as described above.

In this embodiment, the apparatus 130 includes a pair of connectors 150 that connect the body 132 to the two syringes and that traps the head 147 of each nozzle insert 145 within the body. Each connector includes a threaded fitting that mates with threads defined in the open ends of the passageway 133. As the connector 150 is threaded into the passageway it clamps the head 147 of the insert 145 within the body. The connectors 150 also include a Luer fitting 154 for mating with the Luer fitting 11 of each syringe. The Luer fittings 154 define a channel 156 for receiving the syringe tip 14 therein. The connectors 150 may include a thumb wheel 158 to facilitate threading the fittings 152, 154 into their respective mating fittings.

In an alternative configuration, the syringe tip can be provided with external threads to engage the internal threads in the passageway 133 of the body 132. With this alternative, the body can be mounted on the tip 14 without the connector 150, and can directly trap the head 147 of the insert 145 between the body and the end of the syringe tip.

The mixing apparatus 130 demonstrates that a nozzle insert can be provided in both syringes, rather than in one syringe only. The mixing apparatus also contemplates a longer fluid flow path between the syringes than most of the prior embodiments. This longer flow path can provide beneficial mixing characteristics for certain fluid compositions.

In a further modification, a one-piece septum component 180 can be engaged within a mixing apparatus 170, as shown in FIG. 20. The mixing apparatus 170 of FIG. 20 can be configured like the apparatus 80 shown in FIG. 15. In particular, the apparatus defines a flow passageway 171 that is intersected by a septum bore 172. The bore 172 defines an orifice 174, similar to the bore and orifice shown in FIG. 15.

In a modification from this prior embodiment, the septum bore 172 defines a septum seat 176 and an enlarged cavity 178. The septum component 180 includes a septum portion 182 that bears against the septum seat 176 directly above the orifice 174. The component 810 further includes an enlarged flange 186 that is sized to expand into the enlarged cavity 178 when the septum portion is seated on the septum seat. The septum component 180 is formed of a resiliently compressible material, such as SILASTIC®, so that the flange 186 can be compressed to squeeze through upper portion of the bore 172 and then resiliently expand outward into the cavity 178. The flange is configured to hold the septum component 180 within the septum bore 172 and maintain a fluid-tight seal between the septum portion 182 and the septum seat 176.

The septum component 180 defines an open bore 184 that terminates at the septum portion 182. The bore 184 serves as a guide for a syringe, such as the syringe 110 depicted in FIG. 15. The septum material can be readily and sealingly penetrated by the needle 111 to accomplish injection of the additional constituent. The septum component 180 can include a handle 188 that can be manually grasped to insert and remove the component from the mixing apparatus 170.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For example, the nozzle insert 90 can be combined with a mixing apparatus 20 or its variations shown in FIGS. 4-13. The body of any of the mixing apparatuses described above may also be provided with more than one septum orifice 101 to permit simultaneous introduction of two different fluids. As a further alternative, the septum set screw 105 can incorporate a fluid dispensing component, such as an integral syringe or a primer bulb that can be operated to push through the orifice. In certain applications, the septum 103 can be replaced with a valve element, such as a valve flap.

As described above, the syringe-to-syringe mixing systems are hand supported. Gripping elements can be added to the syringes to facilitate gripping of the syringes and manipulation of the syringe plungers. Alternatively, a fixture can be provided to support the syringes and/or mixing apparatus. Furthermore, while the illustrated embodiments contemplate manually operated syringes, the mixing apparatuses and nozzle inserts can also be used with powered fluid dispensing systems.

The principles of the present invention can also be employed to mix granular or particulate constituents with a fluid. In this instance, the granular constituents can be contained in one syringe and the fluid constituent in the other. The nozzle insert can be engaged within the first syringe so that the "jet flow" will agitate the granular material as the fluid is injected.

What is claimed is:

1. An improvement to a syringe-to-syringe mixing apparatus comprising a nozzle element disposed within the internal tip of a syringe, the external tip of said syringe being configured for connection to an apparatus to facilitate mixing, said nozzle element defining a passageway therethrough in communication with the interior volume of the syringe and including a substantially cylindrical restriction in said nozzle element, said passageway having a first portion of gradually decreasing flow area toward and communicating with one end of said restriction, a second portion of gradually increasing flow area away from and communicating with an opposite end of said restriction, and a third portion extending from the end of the tip of said syringe to and communicating with said first portion of said passageway, said nozzle element configured to increase the flow velocity therethrough.

2. The improvement of claim 1, wherein said nozzle element is an insert configured to be mounted in a fixed position within the tip of the syringe.

3. The improvement of claim 2, wherein said insert includes a retaining flange at an opposite end of said nozzle element, said retaining flange configured to engage the end of the syringe tip.

4. The improvement of claim 2, wherein said insert is configured to be inserted into the tip of the syringe through the interior volume of the syringe.

5. The improvement of claim 1, wherein said nozzle element is integrally formed within the tip of the syringe such that said second portion of said passageway opens immediately into the interior of said syringe.

6. The improvement of claim 1, wherein said second portion of said passageway opens immediately into the interior of the interior of said syringe.

7. The improvement of claim 1, wherein the length of the substantially cylindrical restriction along the passageway is less than the length of said third portion along said passageway.

8. The improvement of claim 1, wherein the length of the passageway of said nozzle element is greater than the effective diameter of the substantially cylindrical restriction.

9. The improvement of claim 1, wherein said tip of said syringe comprises a fitting for fluid tight connection to another apparatus.

10. The improvement of claim 9, wherein said fitting comprises external threads.

\* \* \* \* \*